United States Patent
Asano et al.

(10) Patent No.: US 7,361,783 B2
(45) Date of Patent: Apr. 22, 2008

(54) (2S)-2-ETHYLPHENYLPROPIONIC ACID DERIVATIVE

(75) Inventors: Jun Asano, Sugito-machi (JP); Shigeki Isogai, Tokyo (JP); Wataru Hori, Oyama (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/515,176

(22) PCT Filed: May 26, 2003

(86) PCT No.: PCT/JP03/06515

§ 371 (c)(1),
(2), (4) Date: Dec. 29, 2005

(87) PCT Pub. No.: WO03/099766

PCT Pub. Date: Dec. 4, 2003

(65) Prior Publication Data

US 2006/0084702 A1  Apr. 20, 2006

(30) Foreign Application Priority Data

May 27, 2002  (JP) .............................. 2002-151700

(51) Int. Cl.
  *C07C 409/44*  (2006.01)
  *A01N 37/12*  (2006.01)
  *A01N 25/00*  (2006.01)
(52) U.S. Cl. ........................ 562/1; 514/562; 514/784
(58) Field of Classification Search .................... 561/1; 514/784, 562; 562/1
See application file for complete search history.

(56) References Cited

U.S. PATENT DOCUMENTS 6,506,797 B1 * 1/2003 Nomura et al. ............. 514/562

FOREIGN PATENT DOCUMENTS

EP  1 184 366  3/2002
EP  1184366 A1 *  3/2002
WO  WO 00/75103  12/2000

OTHER PUBLICATIONS

See monograph: by Richard B. Silverman The Organic Chemistry of Drug Design and Drug Action, 1992, Academic Press, Inc. Drug Development Lead Modification, 1992, p. No. 20, Table 2.3.*

* cited by examiner

*Primary Examiner*—Yvonne Eyler
*Assistant Examiner*—Lalitha Nagubandi
(74) *Attorney, Agent, or Firm*—Oblon, Spivak, McClelland, Maier & Neustadt, P.C.

(57) ABSTRACT

The invention provides novel (2S)-2-ethylphenylpropanoic acid derivatives that bind to the receptor as ligands of human peroxisome proliferator-activated receptor (PPAR) α to activate and exhibit lipid-lowering effect, inhibitory effect on the arteriosclerosis, antiobesity effect, blood glucose-lowering effect, etc., their addition salts, and their medicinal compositions.

(2S)-2-Ethylphenylpropanoic acid derivatives represented by a general formula (1)

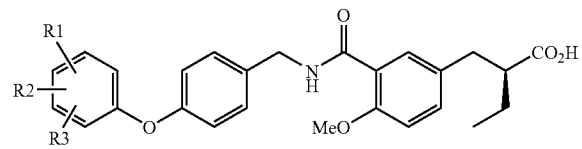

(1)

[wherein R1 denotes a halogen atom or trifluoromethyl group, R2 denotes a hydrogen atom, halogen atom or trifluoromethyl group, and, when R2 denotes a hydrogen atom, R3 denotes a halogen atom or trifluoromethyl group and, when R2 denotes a halogen atom or trifluoromethyl group, R3 denotes a hydrogen atom, halogen atom or trifluoromethyl group], and their addition salts.

19 Claims, No Drawings

(2S)-2-ETHYLPHENYLPROPIONIC ACID DERIVATIVE

TECHNICAL FIELD

The present invention relates to (2S)-2-ethylphenylpropanoic acid derivatives, effective for the therapy of dyslipidemia, diabetes mellitus, etc. as agonists of human peroxisome proliferator-activated receptor(PPAR), in particular, as agonists for human PPARα isoform, their addition salts, and medicinal compositions containing these compounds.

BACKGROUND TECHNOLOGIES

The peroxisome proliferator-activated receptor (PPAR) is a ligand-dependent transcription factor that belongs to nuclear receptor superfamily such as steroid receptor, retinoid receptor and thyroid receptor. Moreover, there exist three isoforms (α type, γ type and δ (or β) type) in this receptor, which are identified in various animal species (Proc. Natl. Acad. Sci., 1992, 89, 4653). Thereamong, the PPARα is distributed in the liver, kidney, etc. with high catabolic capacity for fatty acids (Endocrinology, 1995, 137, 354), positively or negatively controlling the expressions of genes relevant to the metabolism and the intracellular transport of fatty acids (e.g. acyl CoA synthetic enzyme, fatty acid-binding protein and lipoprotein lipase) and apolipo protein (AI, AII, CIII) genes relevant to the metabolisms of cholesterol and triglyceride. The PPARβ is expressed ubiquitously in the tissues of organisms, including nerve cells. The PPARγ is highly expressed in the adipocytes and involved in the differentiation of adipocytes (J. Lipid Res., 1996, 37, 907). At present, the physiological significance of PPARδ is unclear. In this way, each isoform of PPAR is fulfilling specific functions in the particular organs and tissues.

Moreover, it is reported that a knock-out mouse of PPARα exhibits hypertriglyceridemia with ageing and becomes obesity mainly by increasing the white adipose tissues (J. Biol. Chem., 1998, 273, 29577). This strongly suggests the relevance between activation of PPARα and decreasing effect of lipids (cholesterol and triglyceride) in blood.

On the other hand, as the therapeutic drugs for hyperlipidemia used mainly at present, fibrates and statins are known. However, the fibrates have only weak decreasing effect of cholesterol, while the statins have weak decreasing effect of free fatty acids and triglycerides. Moreover, with respect to the fibrates, adverse effects such as gastrointestinal injury, anthema, headache, hepatic disorder, renal disorder and biliary calculus are reported, hence the development of a therapeutic drug for hyperlipidemia due to specific mechanism that exhibits no such adverse effects is desired.

When considering the present situation of such conventional therapeutic drugs for hyperlipidemia, and the role on the regulatory function of lipometabolism and the connection to the pathology of hyperlipidemia of transcription factor called PPARα, which has become clear until now, if a compound that binds directly to PPARα, in particular, to human PPARα as a ligand and is capable of potently activating human PPARα could be created, it would be expected to become a therapeutic drug that exhibits the decreasing effect of lipids (both of cholesterol and triglyceride) in blood due to specific mechanism.

As endogenous ligands of PPARα, eicosanoids in hydroxyeicosatetraenoic acid (HETE) group produced via oxidation with cytochrome P-450, in particular, 8-HETE, 8-HEPE, etc. are reported in addition to LTB$_4$ being a metabolite of arachidonic acid (Proc. Natl. Acad. Sci., 1997, 94, 312). However, these endogenous unsaturated fatty acid derivatives are unstable metabolically and chemically and cannot be offered as medicinal drugs.

On the other hand, as compounds with similar structure to the inventive compounds, for which the agonistic activity on PPARα is reported, compounds represented by a general formula (A)

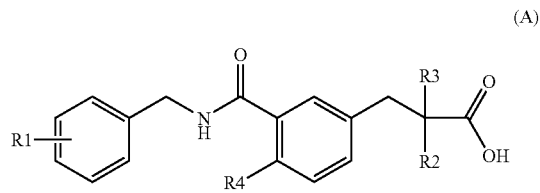

(A)

[wherein R1 denotes a lower alkyl group with carbon atoms of 1 to 4, lower alkoxy group with carbon atoms of 1 to 3, trifluoromethyl group, trifluoromethoxy group, phenyl group which is unsubstituted or which may have substituents, phenoxy group which is unsubstituted or which may have substituents, or benzyloxy group which is unsubstituted or which may have substituents, R2 denotes a lower alkyl group with carbon atoms of 1 to 4, 2,2,2-trifluoroethyl group, lower alkoxy group with carbon atoms of 1 to 3, phenoxy group, lower alkylthio group with carbon atoms of 1 to 3, phenylthio group or benzylthio group, and, when R2 is a lower alkyl group with carbon atoms of 1 to 4 or 2,2,2-trifluoroethyl group, R3 denotes a hydrogen atom or lower alkyl group with carbon atoms of 1 to 4 and, when R2 is a lower alkoxy group with carbon atoms of 1 to 3, phenoxy group, lower alkylthio group with carbon atoms of 1 to 3, phenylthio group or benzylthio group, R3 denotes a hydrogen atom, and R4 denotes a lower alkoxy group with carbon atoms of 1 to 3], in Jpn. Kokai Tokkyo Koho JP 2001/55367, compounds represented by a general formula (B)

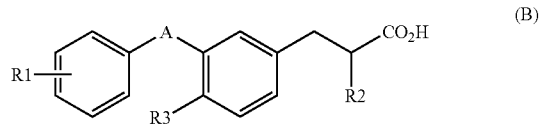

(B)

[wherein R1 denotes a lower alkyl group, lower alkoxy group, trifluoromethyl group, trifluoromethoxy group or benzyloxy group which may have substituents, R2 denotes a hydrogen atom, lower alkyl group or lower alkoxy group, R3 denotes a lower alkoxy group, and A denotes —CH$_2$CONH—, —NHCOCH$_2$—, —CH$_2$CH$_2$CO—, —CH$_2$CH$_2$CH$_2$—, —CH$_2$CH$_2$O—, —CONHCH$_2$—, —CH$_2$NHCH$_2$—, —COCH$_2$O—, —OCH$_2$CO—, —COCH$_2$NH— or —NHCH$_2$CO—], in WO01/92201, and compounds represented by a general formula (C)

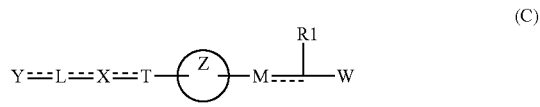

(C)

[wherein R1 denotes a hydrogen atom, hydroxyl group, alkyl group or the like, L denotes a single bond, double bond, alkylene group or the like, M denotes a single bond, alkylene group or the like, T denotes a single bond, alkylene group or the like, W denotes a carboxyl group, group represented by —CON(R11)R12 or the like, ≞denotes a single bond or double bond, X denotes an oxygen atom, alkenylene group or the like, Y denotes an aromatic hydrocarbon group which may have hetero atom, or the like, and ring Z denotes a hydrocarbon group which may have hetero atom], in WO01/251281 are known. However, in the specifications of these patent applications, (2S)-2-ethylphenylpropanoic acid having a group represented by a formula

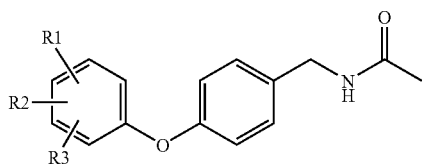

[wherein R1 denotes a halogen atom or trifluoromethyl group, R2 denotes a hydrogen atom, halogen atom or trifluoromethyl group, and, when R2 denotes a hydrogen atom, R3 denotes a halogen atom or trifluoromethyl group and, when R2 denotes a halogen atom or trifluoromethyl group, R3 denotes a hydrogen atom, halogen atom or trifluoromethyl group], being a feature of the inventive compounds, is not disclosed.

The subject of the invention is to provide compounds that have a different structure from that of publicly known compounds aforementioned, that have potent agonistic activity on PPARα and exhibit potent effect in vivo, and further that have excellent properties in the points of safety, persistence, etc.

DISCLOSURE OF THE INVENTION

As a result of diligent studies paying an attention to such specific role on the lipometabolism of human PPARα, aiming at the creation of structurally novel drug with effectiveness, persistence and high safety as a therapeutic drug for hyperlipidemia, the inventors have found that novel (2S)-2-ethylphenylpropanoic acid derivatives and their addition salts of the invention have excellent transcriptional activation on human PPARα, are excellent in the persistence, and exhibit excellent lipid-lowering effect in vivo. Namely, it has been found that (2S)-2-ethylphenylpropanoic acid derivatives represented by a general formula (1)

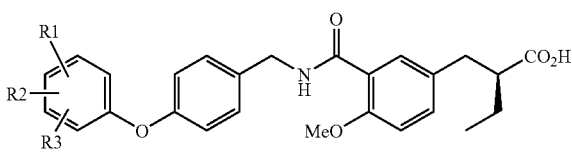

(1)

[wherein R1 denotes a halogen atom or trifluoromethyl group, R2 denotes a hydrogen atom, halogen atom or trifluoromethyl group, and, when R2 denotes a hydrogen atom, R3 denotes a halogen atom or trifluoromethyl group and, when R2 denotes a halogen atom or trifluoromethyl group, R3 denotes a hydrogen atom, halogen atom or trifluoromethyl group], and their addition salts have excellent transcriptional activation on human PPARα, are excellent in the persistence, and exhibit excellent lipid-lowering effect in vivo, leading to the completion of the invention.

Furthermore, it has been found that (2S)-2-ethylphenylpropanoic acid derivatives represented by a general formula (1-a)

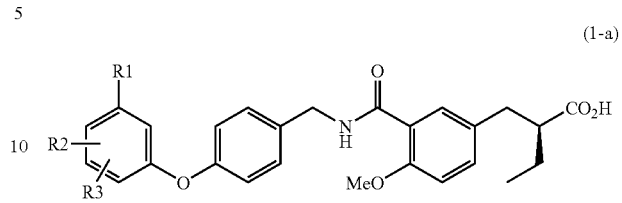

(1-a)

[wherein R1 denotes a halogen atom or trifluoromethyl group, R2 denotes a hydrogen atom, halogen atom or trifluoromethyl group, and, when R2 denotes a hydrogen atom, R3 denotes a halogen atom or trifluoromethyl group and, when R2 denotes a halogen atom or trifluoromethyl group, R3 denotes a hydrogen atom, halogen atom or trifluoromethyl group], and their addition salts have excellent transcriptional activation on human PPARα, are excellent in the persistence, and exhibit excellent lipid-lowering effect in vivo, leading to the completion of the invention.

Still more, it has been found that (2S)-2-ethylphenylpropanoic acid derivatives represented by a general formula (1-b)

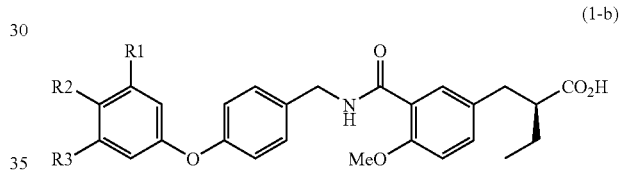

(1-b)

[wherein R1 denotes a halogen atom or trifluoromethyl group, R2 denotes a hydrogen atom, halogen atom or trifluoromethyl group, and, when R2 denotes a hydrogen atom, R3 denotes a halogen atom or trifluoromethyl group and, when R2 denotes a halogen atom or trifluoromethyl group, R3 denotes a hydrogen atom, halogen atom or trifluoromethyl group], and their addition salts have excellent transcriptional activation on human PPARα, are excellent in the persistence, and exhibit excellent lipid-lowering effect in vivo, leading to the completion of the invention.

In the general formula (1) of the inventive compounds, preferably compounds with general formula being (1-a) are mentioned. More preferably, in the general formula (1), compounds with general formula being (1-b) are mentioned. Still more preferably, in the general formula (1-b), compounds with R1 and R3 denoting a halogen atom or trifluoromethyl group and R2 denoting a hydrogen atom, halogen atom or trifluoromethyl group are mentioned.

As these still more preferable compounds, compounds shown below, namely, (2S)-2-{[3-(N-{[4-(3,5-bistrifluoromethylphenoxy)phenyl]methyl}carbamoyl)-4-methoxyphenyl]methyl}butyric acid, (2S)-2-{[3-(N-{[4-(3-bromo-5-chlorophenoxy)phenyl]methyl}carbamoyl)-4-methoxyphenyl]methyl}butyric acid, (2S)-2-{[3-(N-{[4-(3-bromo-5-fluorophenoxy)phenyl]methyl}carbamoyl)-4-methoxyphenyl]methyl}butyric acid, (2S)-2-{[3-(N-{[4-(3-bromo-5-trifluoromethylphenoxy)phenyl]methyl}carbamoyl)-4-methoxyphenyl]methyl}butyric acid, (2S)-2-{[3-(N-{[4-(3-chloro-5-fluorophenoxy)phenyl]methyl}carbamoyl)-4-methoxyphenyl]methyl}butyric acid, (2S)-2-{[3-(N-{[4-(3-chloro-5-trifluoromethylphenoxy)phenyl]methyl}carbamoyl)-4-methoxyphenyl]methyl}butyric acid, (2S)-2-{[3-(N-{[4-(3-fluoro-5-trifluoromethylphenoxy)phenyl]methyl}carbamoyl)-4-methoxyphenyl]methyl}butyric acid, (2S)-2-{[3-(N-{[4-(3,5-dibromophenoxy)phenyl]methyl}carbamoyl)-4-methoxyphenyl]methyl}butyric acid, (2S)-2-{[3-(N-{[4-(3,5-dichlorophenoxy)phenyl]methyl}carbamoyl)-4-methoxyphenyl]methyl}butyric acid, (2S)-2-{[3-(N-{[4-(3,5-difluorophenoxy)phenyl]methyl}carbamoyl)-4-methoxyphenyl]methyl}butyric acid, (2S)-2-{[3-(N-{[4-(3,4,5-trichlorophenoxy)phenyl]methyl}carbamoyl)-4-methoxyphenyl]methyl}butyric acid, (2S)-2-{[3-(N-{[4-(3,4,5-trifluorophenoxy)phenyl]methyl}carbamoyl)-4-methoxyphenyl]methyl}butyric acid, and the like are mentioned.

In the description of general formula (1) of the invention, for "halogen atoms", fluorine, chlorine, bromine and iodine are mentioned. Compounds of the invention can be prepared through processes that follow the processes described in Jpn. Kokai Tokkyo Koho JP 2001/55367, for example, through following processes (Scheme1).

sizable through the processes described in Jpn. Kokai Tokkyo Koho JP 2001/55367 and represented by a general formula (2)

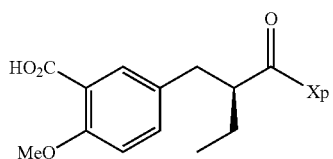

(2)

[wherein Xp denotes a chiral oxazolidinone group such as optically active 4-benzyl-2-oxazolidinone-3-yl group, 4-isopropyl-2-oxazolidinone-3-yl group or 4-phenyl-2-oxazolidinone-3-yl group], with compounds represented by a general formula (3)

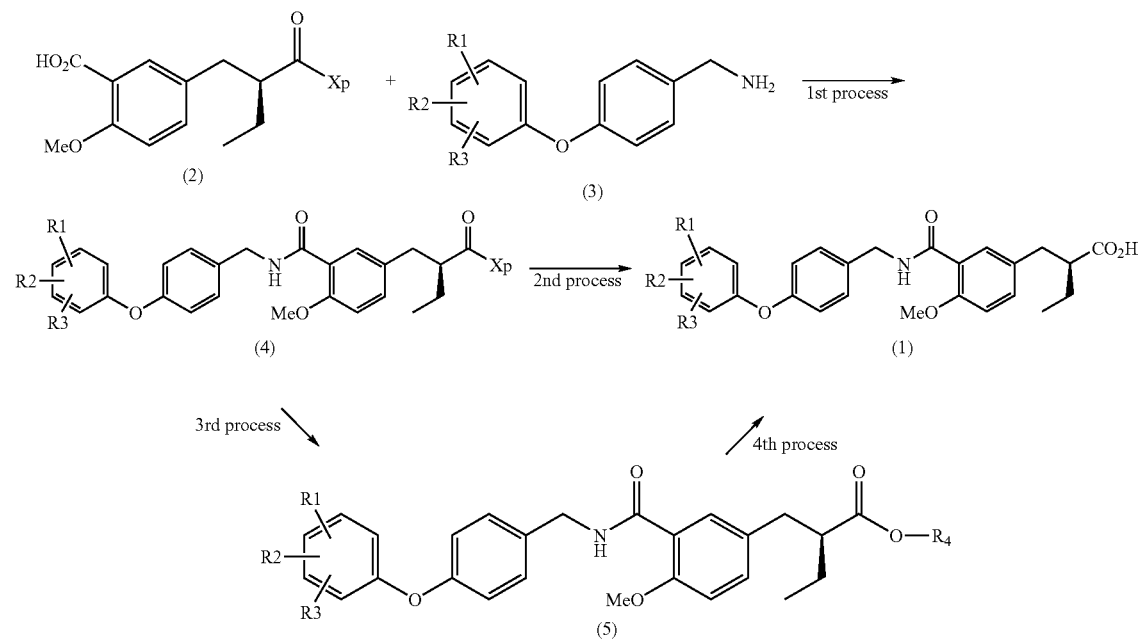

Namely, compounds represented by the general formula (1)

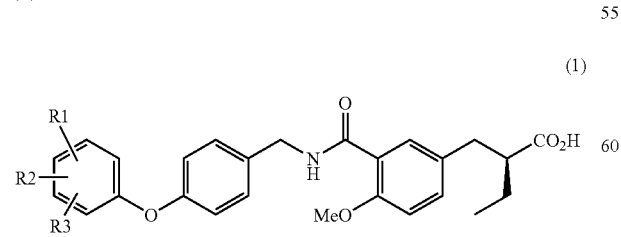

[wherein R1, R2 and R3 are as described above], can be synthesized by reacting (first process) compounds synthe-

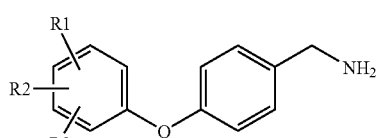

[wherein R1, R2 and R3 are as described above], for 4 to 24 hours at 10 to 80° C. in a suitable solvent, for example, chloroform, dichloromethane or the like, using a suitable condensing agent, for example, dicyclohexylcarbodiimide, N-ethyl-N'-3-dimethylaminopropylcarbodiimide hydrochloride or the like, or by reacting compounds represented by the general formula (2) for 0.5 to 2 hours at −10 to 20° C. in a suitable solvent, for example, chloroform, dichloromethane or the like, using a suitable acid halide or acid anhydride, for example, ethyl chlorocarbonate, trifluoroacetic anhydride or the like, in the presence of suitable base, for example, triethylamine or the like, and then by reacting with compounds represented by the general formula (3), to synthesize compounds represented by a general formula (4)

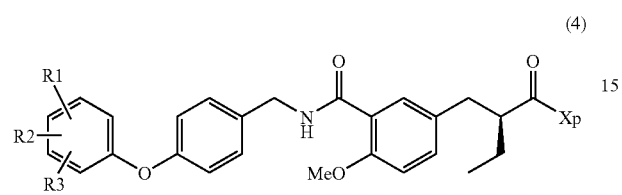

(4)

[wherein R1, R2, R3 and Xp are as described above], and by reacting (second process) these compounds for 0.5 to 8 hours at −20 to 20° C. in a suitable solvent, for example, tetrahydrofuran, dioxane or the like, using hydrogen peroxide and lithium hydroxide. Moreover, compounds represented by the general formula (1) can be synthesized by reacting (third process) compounds shown by the general formula (4) for 0.5 to 8 hours at −20 to 20° C. in a suitable solvent, for example, tetrahydrofuran, dioxane or the like, using hydrogen peroxide and lithium hydroxide, then esterifying through the publicly known esterification process, for example, process for reacting for 0.5 to 4 hours at 0 to 20° C. in methanol, using trimethylsilyldiazomethane, to synthesize compounds represented by a general formula (5)

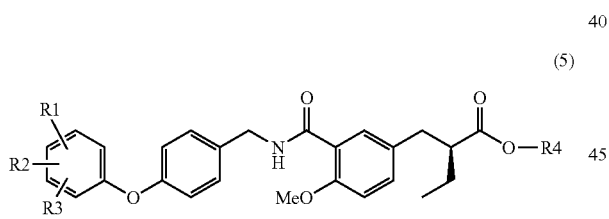

(5)

[wherein R1, R2 and R3 are as described above, and R4 denotes a lower alkyl group with C1~4], and by reacting (fourth process) these compounds for 4 to 48 hours at 20 to 80° C. in a suitable solvent, for example, water, methanol, ethanol, mixed solvent thereof or the like, using a suitable base, for example, potassium hydroxide, sodium hydroxide, lithium hydroxide or the like.

Moreover, compounds represented by the general formula (3) can be synthesized through publicly known processes, for example, processes described in Bioorg. Med. Chem., 1998, 6, 15, Jpn. Kokai Tokkyo Koho JP 003/223256, Jpn. Kokai Tokkyo Koho JP 003/81266, etc., or processes that follow these, for example, through following processes (Scheme 2)

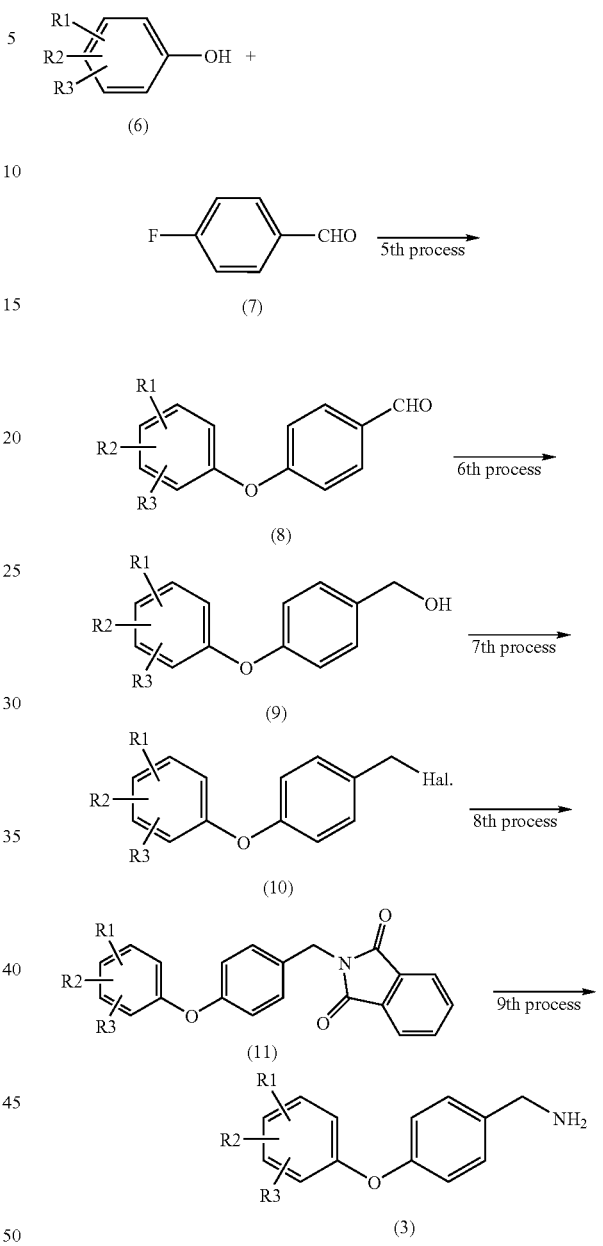

Namely, compounds represented by the general formula (3)

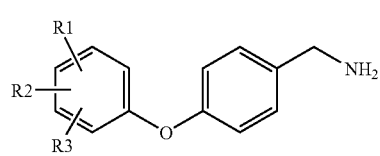

(3)

[wherein R1, R2 and R3 are as described above], can be synthesized by reacting (fifth process) compounds represented by a general formula (6)

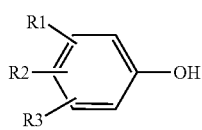

(6)

[wherein R1, R2 and R3 are as described above], with compounds represented by a general formula (7)

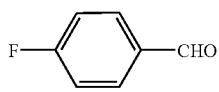

(7)

for 0.5 to 24 hours at 20 to 120° C. without solvent or in a suitable solvent, for example, acetonitrile, N,N-dimethylformamide or the like, in the presence of suitable base, for example, sodium hydride, potassium carbonate, sodium carbonate or the like to synthesize compounds represented by a general formula (8)

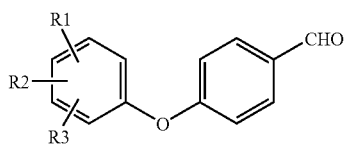

(8)

[wherein R1, R2 and R3 are as described above], by reacting (sixth process) these compounds for 1 to 8 hours at 0 to 80° C. in a suitable solvent, for example, ethanol, isopropanol or the like, using a suitable reducing agent, for example, sodium borohydride, sodium aluminum hydride or the like, to synthesize compounds represented by a general formula (9)

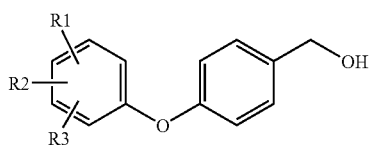

(9)

[wherein R1, R2 and R3 are as described above], by reacting (seventh process) these compounds for 2 to 8 hours at 0 to 80° C. without solvent or in a suitable solvent, for example, chloroform, dichloromethane or the like, using a suitable halogenating agent, for example, thionyl chloride, phosphorus tribromide or the like, to synthesize compounds represented by a general formula (10)

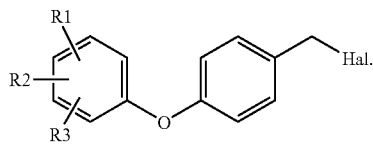

(10)

[wherein R1, R2 and R3 are as described above, and Hal. denotes a chlorine atom or bromine atom], by reacting (eighth process) these compounds with potassium salt of phthalimide for 2 to 48 hours at 20 to 120° C. in a suitable solvent, for example, acetonitrile or N,N-dimethylformamide, to synthesize compounds represented by a general formula (11)

(11)

[wherein R1, R2 and R3 are as described above], and by reacting (ninth process) these compounds for 1.5 to 8 hours at 40 to 100° C. in a suitable solvent, for example, ethanol, isopropanol or the like, using hydrazine-hydrate. As the forms for administering the inventive novel compounds, for example, oral administration with tablets, capsules, granules, powders, inhalants, syrups or the like, or parenteral administration with injections, suppositories or the like can be mentioned.

BEST EMBODIMENT TO PUT THE INVENTION INTO PRACTICE

Examples and referential examples of the inventive compounds will be described below to illustrate the invention in more detail. However, the invention is not confined to these examples, and they may be altered within a range not to deviate from the scope of the invention.

EXAMPLE 1

[3(2S),4R]-4-Benzyl-3-(2-{3-[3-(N-{[4-(3,4-difluorophenoxy)phenyl]methyl}carbamoyl)-4-methoxyphenyl]methyl})butanoyloxazolidinone-2-one

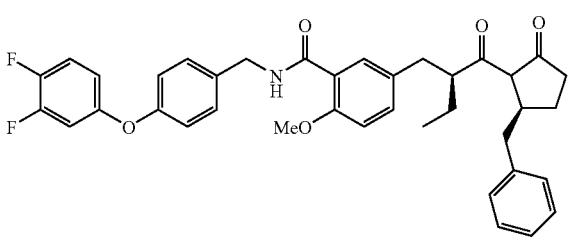

To a solution of compound (500 mg, 1.37 mmol) of Referential example 1 in ethanol (10 mL) was added hydrazine-hydrate (137 mg, 2.74 mmol), and the mixture was refluxed for 2 hours. The reaction mixture was filtered and the filtrate was concentrated under reduced pressure. Ethyl acetate was added to the residue, which was washed with 2 mol/L aqueous solution of sodium hydroxide and brine. The ethyl acetate layer was dried over anhydrous magnesium sulfate and then concentrated. To the residue were added dichloromethane (15 mL), [3(2S),4R]-3-[2-ethyl-3-(4-methoxy-3-{N-[(4-fluorophenoxyphenyl)methyl]carbamoyl}phenyl)propanoyl]-4-benzyloxazolidine-2-one (542 mg, 1.37 mmol) and N-ethyl-N'-3-dimethylaminopropylcarbodiimide hydrochloride (395 mg, 2.06 mmol) in turn, and the mixture was stirred for 14 hours at room temperature. After concentrating the reaction mixture, the residue was purified by silica gel column chromatography (hexane:ethyl acetate=20:1→5:1) to afford 545 mg of white amorphous title compound. Yield 63%.

$^1$H-NMR (400 MHz, CDCl$_3$, δ): 0.92 (3H, t, J 7.8), 1.74-1.81 (1H, m), 2.58 (1H, dd, J 9.2, 13.2), 2.82-2.77 (1H, dd, J 6.8, 13.7), 3.05-3.15 (2H, m), 4.02-4.18 (3H, m), 4.62-4.71 (3H, m), 6.69 (1H, m), 6.78-6.84 (1H, m), 6.90-6.93 (3H, m), 7.06-7.32 (5H, m), 7.43 (1H, dd, J 2.0, 8.3), 8.17 (1H, brt), a CH proton dissolved into H$_2$O.

EXAMPLES 2 THROUGH 8

Through similar process to Example 1, compounds listed in following Table 1 were obtained.

TABLE 1

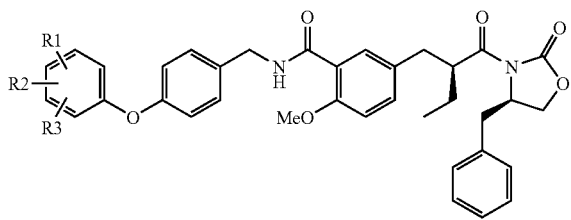

| Example | R1 | R2 | R3 |
|---|---|---|---|
| 2 | 3-F | 5-F | H |
| 3 | 2-F | 3-F | H |
| 4 | 2-F | 4-F | H |
| 5 | 2-F | 5-F | H |
| 6 | 2-F | 6-F | H |
| 7 | 3-F | 4-F | 5-F |
| 8 | 3-CF$_3$ | 5-CF$_3$ | H |

COMPOUND OF EXAMPLE 2

[3(2S),4R]-4-Benzyl-3-(2-{3-[3-(N-{[4-(3,5-difluorophenoxy)phenyl]methyl}carbamoyl)-4-methoxyphenyl]methyl})butanoyloxazolidinone-2-one $^1$H-NMR (400 MHz, CDCl$_3$, δ): 0.93 (3H, t, J 7.3), 1.74-1.81 (1H, m), 2.58 (1H, dd, J 9.3, 13.2), 2.80 (1H, dd, J 6.8, 13.7), 3.06-3.15 (2H, m), 3.91 (3H, s), 4.01-4.18 (3H, m), 4.65 (2H, d, J 5.9), 4.66-4.70 (1H, m), 6.45-6.54 (3H, m), 6.92 (1H, d, J 8.3), 6.98 (2H, d, J 8.8), 7.07 (2H, d, J 6.3), 7.22-7.28 (3H, m), 7.34 (2H, d, J 8.8), 7.43 (1H, dd, J 2.4, 8.3), 8.11 (1H, d, J 2.4), 8.18 (1H, brt).

COMPOUND OF EXAMPLE 3

[3(2S),4R]-4-Benzyl-3-(2-{3-[3-(N-{[4-(2,3-difluorophenoxyl)phenyl]methyl}carbamoyl)-4-methoxyphenyl]methyl})butanoyloxazolidinone-2-one $^1$H-NMR (400 MHz, CDCl$_3$, δ): 0.92 (3H, t, J 7.3), 1.52-1.62 (1H, m), 2.57 (1H, dd, J 9.3, 13.2), 2.80 (1H, dd, J 6.8, 13.7), 3.05-3.14 (2H, m), 3.89 (3H, s), 4.03-4.18 (3H, m), 4.62-4.70 (3H, m), 6.75-6.79 (1H, m), 6.90-7.03 (5H, m), 7.07 (2H, d, J 6.3), 7.20-7.30 (5H, m), 7.42 (1H, dd, J 2.4, 8.8), 8.10 (1H, d, J 2.4), 8.15 (1H, brt).

COMPOUND OF EXAMPLE 4

[3(2S),4R]-4-Benzyl-3-(2-{3-[3-(N-{[4-(2,4-difluorophenoxy)phenyl]methyl}carbamoyl)-4-methoxyphenyl]methyl})butanoyloxazolidinone-2-one $^1$H-NMR (400 MHz, CDCl$_3$, δ): 0.92 (3H, t, J 7.3), 1.54-1.58 (1H, m), 1.75-1.79 (1H, m), 2.57 (1H, dd, J 9.8, 13.7), 2.79 (1H, dd, J 6.8, 13.2), 3.05-3.15 (2H, m), 3.88 (3H, s), 4.02-4.18 (3H, m), 4.61 (2H, d, J 5.9), 4.65-4.70 (1H, m), 6.83-7.08 (8H, m), 7.22-7.28 (5H, m), 7.42 (1H, dd, J 2.4, 8.3), 8.10 (1H, d, J 2.4), 8.13 (1H, brt).

COMPOUND OF EXAMPLE 5

[3(2S),4R]-4-Benzyl-3-(2-{3-[3-(N-{[4-(2,5-difluorophenoxy)phenyl]methyl}carbamoyl)-4-methoxyphenyl]methyl})butanoyloxazolidinone-2-one $^1$H-NMR (400 MHz, CDCl$_3$, δ): 0.92 (3H, t), 1.74-1.81 (1H, m), 2.57 (1H, dd, J 9.3, 13.7), 2.80 (1H, dd, J 6.8, 13.2), 3.05-3.15 (2H, m), 3.89 (3H, s), 4.01-4.18 (3H, m), 4.62-4.70 (3H, m), 6.68-6.73 (1H, m), 6.75-6.81 (1H, m), 6.91 (1H, d, J 8.8), 6.94 (2H, d, J 8.8), 7.07 (2H, d, J 6.3), 7.09-7.15 (1H, m), 7.22-7.31 (5H, m), 7.43 (1H, dd, J 2.4, 8.8), 8.10 (1H, d, J 2.4), 8.15 (1H, brt), a CH proton dissolved into H$_2$O.

COMPOUND OF EXAMPLE 6

[3(2S),4R]-4-Benzyl-3-(2-{3-[3-(N-{[4-(2,6-difluorophenoxy)phenyl]methyl}carbamoyl)-4-methoxyphenyl]methyl})butanoyloxazolidinone-2-one $^1$H-NMR (400 MHz, CDCl$_3$, δ): 0.92 (3H, t), 1.73-1.81 (1H, m), 2.56 (1H, dd, J 9.8, 13.7), 2.79 (1H, dd, J 6.3, 13.2), 3.05-3.14 (2H, m), 3.87 (3H, s), 4.00-4.18 (3H, m), 4.60 (2H, d, J 5.9), 4.64-4.70 (1H, m), 6.86-6.91 (3H, m), 6.98-7.07 (4H, m), 7.12-7.24 (6H, m), 7.42 (1H, dd, J2.4, 8.8), 8.09-8.11 (2H, m), a CH proton dissolved into H$_2$O.

COMPOUND OF EXAMPLE 7

[3(2S),4R]-4-Benzyl-3-(2-{[4-methoxy-3-(N-{[4-(3,4,5-trifluorophenoxy)phenyl]methyl}carbamoyl)phenyl]methyl})butanoyl oxazolidinone-2-one $^1$H-NMR (400 MHz, CDCl$_3$, δ): 0.92 (3H, t, J 7.3), 1.72-1.83 (1H, m), 2.58 (1H, dd, J 9.8, 13.7), 2.80 (1H, dd, J 6.8, 13.7), 3.06-3.15 (2H, m), 3.91 (3H, s), 4.01-4.18 (3H, m), 4.60-4.71 (3H, m), 6.56-6.61 (2H, m), 6.91-6.95 (3H, m), 7.07 (2H, d, J 6.8), 7.22-7.28 (3H, m), 7.33 (2H, d, J 8.8), 7.43 (1H, dd, J 2.4, 8.8), 8.11 (1H, d, J 2.4), 8.19 (1H, brt), a CH proton dissolved into H$_2$O.

COMPOUND OF EXAMPLE 8

[3(2S),4R]-4-Benzyl-3-[2-({3-[N-({4-[3,5-bis(trifluoromethyl)phenoxy]phenyl}methyl)carbamoyl]-4-methoxyphenyl}methyl)]butanoyloxazolidinone-2-one $^1$H-NMR (400 MHz, CDCl$_3$, δ): 0.93 (3H, t, J 7.3), 1.52-1.63 (1H, m), 1.72-1.81 (1H, m), 2.58 (1H, dd, J 9.3, 13.2), 2.80 (1H, dd, J 6.8, 13.7), 3.06-3.15 (2H, m), 3.91 (3H, s), 4.01-4.18 (3H, m), 4.66-4.70 (3H, m), 6.92 (1H, d, J 8.3), 6.98 (2H, d, J 8.3), 7.07 (2H, d, J 6.3), 7.20-7.28 (3H, m), 7.36-7.38 (4H, m), 7.44 (1H, dd, J 2.4, 8.3), 7.56 (1H, s), 8.11 (1H, d, J 2.4), 8.21 (1H, brt).

EXAMPLE 9

(2S)-2-{[3-(N-{[4-(3,4-Difluorophenoxy)phenyl]methyl}carbamoyl)-4-methoxyphenyl]methyl}butyric acid

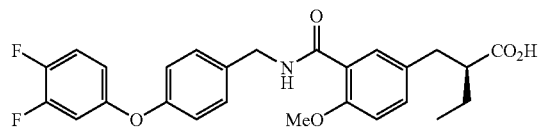

To a solution of compound (545 mg, 0.867 mmol) of Example 1 in tetrahydrofuran (5 mL) was added water (1 mL), which was cooled to 0° C. To this were added 30% aqueous hydrogen peroxide (411 mg, 3.63 mmol) and 1 mol/L aqueous solution of lithium hydroxide (1.45 mL) in turn, and the mixture was stirred for 2 hours at 0° C. To the reaction mixture was added a 64% solution of sodium hydrogensulfite (590 mg) in water (2 mL), and the mixture was stirred for 30 minutes at 0° C. The reaction mixture was brought to pH 3 with 3 mol/L hydrochloric acid, which was extracted with ethyl acetate. The ethyl acetate layer was washed with brine, dried over anhydrous magnesium sulfate, and then concentrated. The residue was purified by silica gel column chromatography (hexane:ethyl acetate=4:1→3:2) to afford 299 mg of white powdery title compound. Yield 73%.

Mp: 118-120° C. $^1$H-NMR (400 MHz, CDCl$_3$, δ): 0.97 (3H, t, J 7.3), 1.56-1.72 (2H, m), 2.59-2.66 (1H, m), 2.80 (1H, dd, J 6.3, 13.8), 2.94 (1H, dd, J 8.3, 13.7), 3.91 (3H, s), 4.65 (2H, d, J 5.9), 4.65 (2H, d, J 5.9), 6.69-6.74 (1H, m), 6.79-6.85 (1H, m), 6.90 (1H, d, J 8.3), 6.97 (2H, d, J 8.8), 7.10 (1H, q, J 9.3), 7.29-7.31 (1H, m), 7.35 (2H, d, J 8.8), 8.07 (1H, d, J 2.4), 8.26 (1H, brt). HRMS: found 469.1666 (−3.5 mmu). Anal: Calcd for C$_{26}$H$_{25}$F$_2$NO$_5$C, 66.52; H, 5.37; N, 2.98; found C, 66.36; H, 5.47; N, 3.22. [α]$_D^{26.0}$: +29.2°.

EXAMPLES 10 THROUGH 15

Using the compounds of Examples 2 through 6 and 8, through similar process to Example 9, compounds listed in following Table 2 were obtained.

TABLE 2

| Example | R1 | R2 |
|---|---|---|
| 10 | 3-F | 5-F |
| 11 | 2-F | 3-F |
| 12 | 2-F | 4-F |
| 13 | 2-F | 5-F |
| 14 | 2-F | 6-F |
| 15 | 3-CF$_3$ | 5-CF$_3$ |

COMPOUND OF EXAMPLE 10

(2S)-2-{[3-(N-{[4-(3,5-Difluorophenoxy)phenyl]methyl}carbamoyl)-4-methoxyphenyl]methyl}butyric acid Mp: 140-142° C. $^1$H-NMR (400 MHz, CDCl$_3$, δ): 0.97 (3H, t, J 7.3), 1.56-1.71 (2H, m), 2.59-2.67 (1H, m), 2.80 (1H, dd, J 6.3, 13.7), 2.95 (1H, dd, J 8.3, 13.7), 3.92 (3H, s), 4.67 (2H, d, J 5.9), 6.46-6.54 (3H, m), 6.90 (1H, d, J 8.3), 7.03 (2H, d, J 8.3), 7.26-7.30 (1H, m), 7.38 (2H, d, J 8.3), 8.08 (1H, d, J 2.4), 8.28 (1H, brt). HRMS: found 469.1681 (−2.0 mmu). Anal: Calcd for C$_{26}$H$_{25}$F$_2$NO$_5$C, 66.52; H, 5.37; N, 2.98; found C, 66.25; H, 5.45; N, 3.12. [α]$_D^{26.3}$: +25.8°.

COMPOUND OF EXAMPLE 11

(2S)-2-{[3-(N-{[4-(2,3-Difluorophenoxy)phenyl]methyl}carbamoyl)-4-methoxyphenyl]methyl}butyric acid Mp: 93-95° C. $^1$H-NMR (400 MHz, CDCl$_3$, δ): 0.97 (3H, t, J 7.3), 1.55-1.70 (2H, m), 2.58-2.66 (1H, m), 2.79 (1H, dd, J 6.3, 13.7), 2.94 (1H, dd, J 8.3, 13.7), 3.91 (3H, s), 4.65 (2H, d, J 5.9), 6.76-6.81 (1H, m), 6.89 (1H, d, J 8.8), 6.91-7.03 (4H, m), 7.28-7.30 (1H, m), 7.33 (2H, d, J 8.8), 8.06 (1H, d, J 2.0), 8.24 (1H, brt). HRMS: found 469.1657 (−4.4 mmu). [α]$_D^{28.7}$:+28.6°.

COMPOUND OF EXAMPLE 12

(2S)-2-{[3-(N-{[4-(2,4-Difluorophenoxy)phenyl]methyl}carbamoyl)-4-methoxyphenyl]methyl}butyric acid—0.3 hydrate Mp: 120-122° C. $^1$H-NMR (400 MHz, CDCl$_3$, δ): 0.97 (3H, t, J 7.3), 1.55-1.67 (2H, m), 2.58-2.65 (1H, m), 2.79 (1H, dd, J 5.9, 13.7), 2.94 (1H, dd, J 8.8, 13.7), 3.90 (3H, s), 4.63 (2H, d, J 5.9), 6.82-6.98 (5H, m), 7.03-7.08 (1H, m), 7.28-7.32 (3H, m), 8.06 (1H, d, J 2.4), 8.22 (1H, brt). HRMS: found 469.1657 (−4.4 mmu). Anal: Calcd for C$_{26}$H$_{25}$F$_2$NO$_5$—0.3H$_2$O C, 65.76; H, 5.43; N, 2.94; found C, 65.73; H, 5.50; N, 3.18. [α]$_D^{28.9}$+26.3°.

COMPOUND OF EXAMPLE 13

(2S)-2-{[3-(N-{[4-(2,5-Difluorophenoxy)phenyl]methyl}carbamoyl)-4-methoxyphenyl]methyl}butyric acid Mp: 116-118° C. $^1$H-NMR (400 MHz, CDCl$_3$, δ): 0.97 (3H, t, J 7.3), 1.56-1.72 (2H, m), 2.60 (1H, m), 2.79 (1H, dd, J 6.3, 13.7), 2.79 (1H, dd, J 6.3, 13.7), 2.95 (1H, dd, J 8.8, 13.7), 3.91 (3H, s), 4.66 (2H, d, J 5.9), 6.70-6.81 (2H, m), 6.89 (1H, d, J 8.3), 6.99 (2H, d, J 8.8), 7.09-7.15 (1H, m), 7.29 (1H, m), 7.35 (2H, d, J 8.8), 8.08 (1H, d, J 2.4), 8.24 (1H, brt). HRMS: found 469.1709 (+0.8 mmu). Anal: Calcd for C$_{26}$H$_{25}$F$_2$NO$_5$ C, 66.52; H, 5.37; N, 2.98; found C, 66.31; H, 5.44; N, 3.25. [α]$_D^{29.0}$:+24.1°.

COMPOUND OF EXAMPLE 14

(2S)-2-{[3-(N-{[4-(2,6-Difluorophenoxy)phenyl]methyl}carbamoyl)-4-methoxyphenyl]methyl}butyric acid Mp: 106-108° C. $^1$H-NMR (400 MHz, CDCl$_3$, δ): 0.96 (3H, t, J 7.8), 1.55-1.71 (2H, m), 2.59-2.66 (1H, m), 2.78 (1H, dd, J 8.3, 13.7), 2.94 (1H, dd, J 8.3, 13.7), 3.89 (3H, s), 4.62 (2H, d, J 5.4), 6.87-6.93 (3H, m), 7.01 (2H, t, J 8.3), 7.11-7.19 (1H, m), 7.27-7.30 (1H, m), 8.06 (1H, d, J 2.0), 8.18 (1H, brt). HRMS: found 469.1669 (−3.2 mmu). Anal: Calcd for C$_{26}$H$_{25}$F$_2$NO$_5$ C, 66.52; H, 5.37; N, 2.98; found C, 66.40; H, 5.39; N, 3.01. [α]$_D^{29.0}$: +27.6°.

COMPOUND OF EXAMPLE 15

(2S)-2-({3-[N-({4-[3,5-Bis(trifluoromethyl)phenoxy]phenyl}methyl)carbamoyl]-4-methoxyphenyl}methyl)butyric acid Mp: 125-127° C. $^1$H-NMR (400 MHz, CDCl$_3$, δ): 0.97 (3H, t, J 7.8), 1.56-1.71 (2H, m), 2.59-2.67 (1H, m), 2.80 (1H, dd, J 6.3, 13.7), 2.95 (1H, dd, J 8.8, 13.7), 3.93 (3H, s), 4.70 (2H, d, J 5.9), 6.91 (1H, d, J 8.3), 7.04 (2H, d, J 8.3), 7.29 (1H, dd, J 2.0, 8.3), 7.38 (2H, s), 7.42 (2H, d, J 8.3), 7.56 (1H, s), 8.08 (1H, d, J 2.0), 8.30 (1H, brt). HRMS: found 569.1655 (+1.8 mmu). Anal: Calcd for C$_{28}$H$_{25}$F$_6$NO$_5$ C, 59.05; H, 4.42; N, 2.46; found C, 59.12; H, 4.43; N, 2.59. [α]$_D^{29.1}$: +20.7°.

EXAMPLE 16

Methyl (2S)-2-{[4-methoxy-3-(N-{[4-(3,4,5-trifluorophenoxy)phenyl]methyl}carbamoyl)phenyl]methyl}butyrate

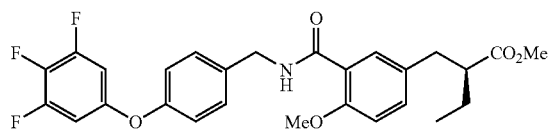

To a solution of compound (700 mg, 1.08 mmol) of Example 7 in tetrahydrofuran (5 mL) was added water (1 mL), which was cooled to 0° C. To this were added 30% aqueous hydrogen peroxide (490 mg, 4.32 mmol) and 1 mol/L aqueous solution of lithium hydroxide (1.73 mL) in turn, and the mixture was stirred for 2 hours at 0° C. To the reaction mixture was added a 64% solution of sodium hydrogensulfite (702 mg) in water (2 mL), and the mixture was stirred for 30 minutes at 0° C. The reaction mixture was brought to pH 3 with 3 mol/L hydrochloric acid, which was extracted with ethyl acetate. The ethyl acetate layer was washed with brine, dried over anhydrous magnesium sulfate, and then concentrated. To the residue were added ethyl acetate (5 mL) and methanol (5 mL), which was cooled to 0° C. Then, 2 mol/L n-hexane solution (0.865 mL) of trimethylsilyldiazomethane was added dropwise under stirring. After completion of the dropwise addition, the mixture was stirred for 2 hours at 0° C. After acetic acid was added to the reaction mixture until yellow color of reaction mixture disappeared, the reaction mixture was concentrated under reduced pressure. The residue was purified by silica gel column chromatography (hexane:ethyl acetate=10:1→2:1) to afford 465 mg of colorless liquid title compound. Yield 86%.

$^1$H-NMR (400 MHz, CDCl$_3$, δ): 0.91 (3H, t, J 7.3), 1.56-1.69 (2H, m), 2.57-2.64 (2H, m), 2.75 (1H, dd, J 6.3, 13.7), 2.93 (1H, dd, J 8.8, 13.7), 3.62 (3H, s), 3.92 (3H, s), 4.67 (2H, d, J 5.9), 6.57-6.61 (2H, m), 6.89 (1H, d, J 8.8), 6.99 (2H, d, J 8.3), 7.25 (1H, dd, J 2.4, 8.8), 7.38 (2H, d, J 8.3), 8.06 (1H, d, J 2.4), 8.26 (1H, brt).

EXAMPLE 17

(2S)-2-{[4-Methoxy-3-(N-{[4-(3,4,5-trifluorophenoxy)phenyl]methyl}carbamoyl)phenyl]methyl}butyric acid

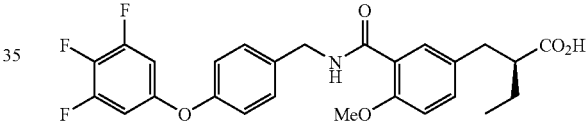

To a solution of compound (465 mg, 0.927 mmol) of Example 16 in methanol (9 mL) were added 1 mol/L aqueous solution of lithium hydroxide (2.04 mL) and water (3 mL), and the mixture was stirred for 4 hours at room temperature. The reaction mixture was allowed to stand statically for 2 days and then stirred for 18 hours at 50° C. Water was added to the reaction mixture, which was filtered. After the filtrate was cooled to 0° C., it was brought to pH 4 with 3 mol/L hydrochloric acid. The precipitated powder was collected by filtration, dried and submitted to silica gel column chromatography (hexane:ethyl acetate=10:1→2:1) to afford 289 mg of crude powder. This was purified by recrystallization (acetonitrile) to afford 183 mg of white powdery title compound. Yield 40%.

Mp: 133-135° C. $^1$H-NMR (400 MHz, CDCl$_3$, δ): 0.97 (3H, t, J 7.8), 1.56-1.71 (2H, m), 2.60-2.67 (1H, m), 2.80 (1H, dd, J 6.3, 13.7), 2.95 (1H, dd, J 8.3, 13.7), 3.92 (3H, s), 4.67 (2H, d, J 5.9), 6.57-6.61 (2H, m), 6.90 (1H, d, J 8.3), 6.99 (2H, d, J 8.8), 7.29 (1H, dd, J 2.4, 8.3), 7.38 (2H, d, J 8.8), 8.08 (1H, d, J 2.4), 8.27 (1H, brt). HRMS: found 487.1574 (−3.3 mmu). Anal: Calcd for C$_{26}$H$_{24}$F$_3$NO$_5$C, 64.06; H, 4.96; N, 2.87; found C, 64.74; H, 4.85; N, 2.93. [α]$_D^{26.8}$: +28.5°.

EXAMPLES 18 THROUGH 23

Using the compounds of Referential examples 9 through 14, through similar process to Example 1, compounds list in following Table 3 were obtained.

TABLE 3

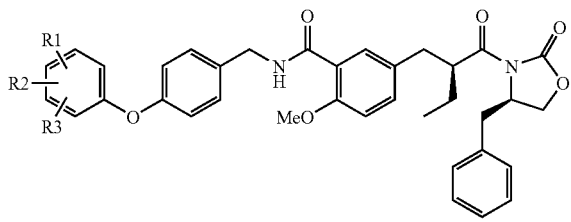

| Example | R1 | R2 | R3 |
|---|---|---|---|
| 18 | 3-Cl | 5-Cl | H |
| 19 | 3-Cl | 4-Cl | H |
| 20 | 3-F | 4-Cl | H |
| 21 | 3-Cl | 4-Br | H |
| 22 | 3-CF$_3$ | 4-Cl | H |
| 23 | 3-CF$_3$ | 5-F | H |

COMPOUND OF EXAMPLE 18

[3(2S),4R]-4-Benzyl-3-(2-{3-[3-(N-{[4-(3,5-dichlorophenoxy)phenyl]methyl}carbamoyl)-4-methoxyphenyl]methyl})butanoyloxazolidinone-2-one $^1$H-NMR (400 MHz, CDCl$_3$, δ): 0.93 (3H, t, J 7.2), 1.54-1.57 (1H, m), 1.76-1.78 (1H, m), 2.57 (1H, dd, J 8.8, 13.6), 2.80 (1H, dd, J 6.8, 13.6), 3.05-3.15 (2H, m), 3.91 (3H, s), 4.03-4.18 (3H, m), 4.64-4.68 (3H, m), 6.84-6.85 (2H, m), 6.91-6.96 (3H, m), 7.06-7.08 (3H, m), 7.22-7.28 (3H, m), 7.32-7.34 (2H, m), 7.42-7.45 (1H, m), 8.11-8.12 (1H, m), 8.18 (1H, brs).

COMPOUND OF EXAMPLE 19

[3(2S),4R]-4-Benzyl-3-(2-{3-[3-(N-{[4-(3,4-dichlorophenoxy)phenyl methyl}carbamoyl)-4-methoxyphenyl]methyl})butanoyloxazolidinone-2-one $^1$H-NMR (400 MHz, CDCl$_3$, δ): 0.92 (3H, t, J 7.4), 1.53-1.60 (1H, m), 1.74-1.79 (1H, m), 2.57 (1H, dd, J 9.2, 13.6), 2.80 (1H, dd, J 6.8, 13.6), 3.05-3.15 (2H, m), 3.90 (3H, s), 4.03-4.18 (3H, m), 4.63-4.70 (3H, m), 6.82-6.85 (1H, m), 6.91-6.96 (3H, m), 7.06-7.08 (3H, m), 7.20-7.29 (3H, m), 7.30-7.38 (3H, m), 7.42-7.44 (1H, m), 8.10-8.11 (1H, m), 8.17 (1H, brs).

COMPOUND OF EXAMPLE 20

[3(2S),4R]-4-Benzyl-3-(2-{3-[3-(N-{[4-(4-chloro-3-fluorophenoxy)phenyl]methyl}carbamoyl)-4-methoxyphenyl]methyl})butanoyloxazolidinone-2-one $^1$H-NMR (400 MHz, CDCl$_3$, δ): 0.92 (3H, t, J 7.2), 1.52-1.60 (1H, m), 1.74-1.79 (1H, m), 2.58 (1H, dd, J 9.6, 13.6), 2.80 (1H, dd, J 6.8, 13.6), 3.05-3.15 (2H, m), 3.90 (3H, s), 4.03-4.18 (3H, m), 4.63-4.70 (3H, m), 6.71-6.78 (2H, m), 6.91-6.96 (3H, m), 7.06-7.08 (2H, m), 7.22-7.33 (6H, m), 7.42-7.44 (1H, m), 8.10-8.11 (1H, m), 8.17 (1H, brs).

COMPOUND OF EXAMPLE 21

[3(2S),4R]-4-Benzyl-3-(2-{3-[3-(N-{[4-(4-bromo-3-chlorophenoxy)phenyl]methyl}carbamoyl)-4-methoxyphenyl]methyl})butanoyloxazolidinone-2-one $^1$H-NMR (400 MHz, CDCl$_3$, δ): 0.92 (3H, t, J 7.2), 1.53-1.60 (1H, m), 1.74-1.79 (1H, m), 2.57 (1H, dd, J 8.8, 13.6), 2.80 (1H, dd, J 6.8, 13.6), 3.05-3.15 (2H, m), 3.90 (3H, s), 4.03-4.18 (3H, m), 4.63-4.70 (3H, m), 6.75-6.78 (1H, m), 6.91-6.95 (3H, m), 7.06-7.08 (3H, m), 7.20-7.33 (5H, m), 7.42-7.44 (1H, m), 7.51-7.53 (1H, m), 8.10-8.11 (1H, m), 8.17 (1H, brs).

COMPOUND OF EXAMPLE 22

[3(2S),4R]-4-Benzyl-3-(2-{3-[3-(N-{[4-(4-chloro-3-trifluoromethylphenoxy)phenyl]methyl}carbamoyl)-4-methoxyphenyl]methyl})butanoyloxazolidinone-2-one $^1$H-NMR (400 MHz, CDCl$_3$, δ): 0.92 (3H, t, J 7.2), 1.52-1.60 (1H, m), 1.74-1.81 (1H, m), 2.58 (1H, dd, J 9.2, 13.6), 2.80 (1H, dd, J 6.8, 13.6), 3.05-3.15 (2H, m), 3.90 (3H, s), 4.03-4.18 (3H, m), 4.64-4.70 (3H, m), 6.91-6.96 (3H, m), 7.04-7.08 (3H, m), 7.20-7.28 (3H, m), 7.30-7.34 (3H, m), 7.41-7.44 (2H, m), 8.10-8.11 (1H, m), 8.18 (1H, brs).

COMPOUND OF EXAMPLE 23

[3(2S),4R]-4-Benzyl-3-(2-{3-[3-(N-{[4-(3-fluoro-5-trifluoromethylphenoxy)phenyl]methyl}carbamoyl)-4-methoxyphenyl]methyl})butanoyloxazolidinone-2-one $^1$H-NMR (400 MHz, CDCl$_3$, δ): 0.92 (3H, t, J 7.2), 1.52-1.56 (1H, m), 1.74-1.81 (1H, m), 2.58 (1H, dd, J 9.6, 13.6), 2.80 (1H, dd, J 6.8, 13.6), 3.06-3.15 (2H, m), 3.91 (3H, s), 4.03-4.18 (3H, m), 4.65-4.70 (3H, m), 6.80-6.83 (1H, m), 6.91-7.08 (7H, m), 7.20-7.28 (3H, m), 7.34-7.36 (2H, m), 7.42-7.45 (1H, m), 8.11 (1H, m), 8.19 (1H, brs).

EXAMPLES 24 THROUGH 29

Using the compounds of Examples 18 through 23, through similar process to Example 16, compounds list in following Table 4 were obtained.

TABLE 4

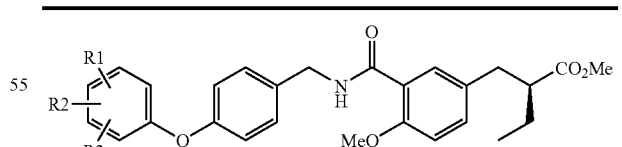

| Example | R1 | R2 | R3 |
|---|---|---|---|
| 24 | 3-Cl | 5-Cl | H |
| 25 | 3-Cl | 4-Cl | H |
| 26 | 3-F | 4-Cl | H |
| 27 | 3-Cl | 4-Br | H |
| 28 | 3-CF$_3$ | 4-Cl | H |
| 29 | 3-CF$_3$ | 5-F | H |

COMPOUND OF EXAMPLE 24

Methyl(2S)-2-{[4-methoxy-3-(N-{[4-(3,5-dichlorophenoxy)phenyl]methyl}carbamoyl)]phenyl]methyl}butyrate $^1$-NMR (400 MHz, CDCl$_3$, δ): 0.91 (3H, t, J 7.4), 1.52-1.69 (2H, m), 2.59-2.64 (1H, m), 2.75 (1H, dd, J 6.4, 14.0), 2.93 (1H, dd, J 8.8, 14.0), 3.62 (3H, s), 3.92 (3H, s), 4.68 (2H, d, J 6.0), 6.85-6.86 (2H, m), 6.88-6.90 (1H, m), 7.00-7.02 (2H, m), 7.06-7.07 (1H, m), 7.23-7.25 (1H, m), 7.37-7.40 (2H, m), 8.06 (1H, m), 8.26 (1H, brs).

COMPOUND OF EXAMPLE 25

Methyl(2S)-2-{[4-methoxy-3-(N-{[4-(3,4-dichlorophenoxy)phenyl]methyl}carbamoyl)phenyl]methyl}butyrate $^1$-NMR (400 MHz, CDCl$_3$, δ): 0.91 (3H, t, J 7.2), 1.52-1.69 (2H, m), 2.58-2.63 (1H, m), 2.75 (1H, dd, J 6.8, 13.6), 2.93 (1H, dd, J 8.8, 13.6), 3.62 (3H, s), 3.92 (3H, s), 4.67 (2H, d, J 5.6), 6.83-6.90 (2H, m), 6.97-7.01 (2H, m), 7.07 (1H, m), 7.23-7.26 (1H, m), 7.35-7.38 (3H, m), 8.05-8.06 (1H, m), 8.25 (1H, brs).

COMPOUND OF EXAMPLE 26

Methyl (2S)-2-{[4-methoxy-3-(N-{[4-(4-chloro-3-fluorophenoxy)phenyl]methyl}carbamoyl)phenyl]methyl}butyrate $^1$H-NMR (400 MHz, CDCl$_3$, δ): 0.91 (3H, t, J 7.6), 1.52-1.67 (2H, m), 2.58-2.63 (1H, m), 2.75 (1H, dd, J 6.8, 14.0), 2.93 (1H, dd, J 8.4, 14.0), 3.62 (3H, s), 3.92 (3H, s), 4.67 (2H, d, J 5.6), 6.71-6.79 (2H, m), 6.88-6.90 (1H, m), 6.98-7.02 (2H, m), 7.23-7.33 (2H, m), 7.35-7.38 (2H, m), 8.05-8.06 (1H, m), 8.25 (1H, brs).

COMPOUND OF EXAMPLE 27

Methyl (2S)-2-{[4-methoxy-3-(N-{[4-(4-bromo-3-chlorophenoxy)phenyl]methyl}carbamoyl)phenyl]methyl}butyrate $^1$H-NMR (400 MHz, CDCl$_3$, δ): 0.91 (3H, t, J 7.2), 1.49-1.70 (2H, m), 2.57-2.64 (1H, m), 2.75 (1H, dd, J 6.4, 13.6), 2.93 (1H, dd, J 8.8, 13.6), 3.62 (3H, s), 3.92 (3H, s), 4.67 (2H, d, J 6.4), 6.76-6.79 (1H, m), 6.88-6.90 (1H, m), 6.97-7.01 (2H, m), 7.07-7.08 (1H, m), 7.23-7.36 (1H, m), 7.36-7.38 (2H, m), 7.51-7.53 (1H, m), 8.05-8.06 (1H, m), 8.25 (1H, brs).

COMPOUND OF EXAMPLE 28

Methyl (2S)-2-{[4-methoxy-3-(N-{[4-(4-chloro-3-trifluoromethylphenoxy)phenyl]methyl}carbamoyl)phenyl]methyl}butyrate $^1$H-NMR (400 MHz, CDCl$_3$, δ): 0.91 (3H, t, J 7.6), 1.52-1.69 (2H, m), 2.59-2.64 (1H, m), 2.75 (1H, dd, J 6.4, 13.6), 2.93 (1H, dd, J 8.8, 13.6), 3.62 (3H, s), 3.92 (3H, s), 4.67 (2H, d, J 5.6), 6.88-6.90 (1H, m), 6.98-7.00 (2H, m), 7.05-7.08 (1H, m), 7.23-7.32 (2H, m), 7.37-7.43 (3H, m), 8.05-8.06 (1H, m), 8.26 (1H, brs).

COMPOUND OF EXAMPLE 29

Methyl (2S)-2-{[4-methoxy-3-(N-{[4-(3-fluoro-5-trifluoromethylphenoxy)phenyl]methyl}carbamoyl)phenyl]methyl}butyrate $^1$H-NMR (400 MHz, CDCl$_3$, δ): 0.91 (3H, t, J 7.2), 1.49-1.69 (2H, m), 2.59-2.64 (1H, m), 2.76 (1H, dd, J 6.4, 14.0), 2.93 (1H, dd, J 8.4, 14.0), 3.63 (3H, s), 3.92 (3H, s), 4.69 (2H, d, J 5.6), 6.81-6.85 (1H, m), 6.88-6.90 (1H, m), 7.00-7.05 (4H, m), 7.22-7.24 (1H, m), 7.40-7.42 (2H, m), 8.06-8.07 (1H, m), 8.27 (1H, brs).

EXAMPLES 30 THROUGH 35

Using the compounds of Examples 24 through 29, through similar process to Example 17, compounds list in following Table 5 were obtained.

TABLE 5

| Example | R1 | R2 | R3 |
|---|---|---|---|
| 30 | 3-Cl | 5-Cl | H |
| 31 | 3-Cl | 4-Cl | H |
| 32 | 3-F | 4-Cl | H |
| 33 | 3-Cl | 4-Br | H |
| 34 | 3-CF$_3$ | 4-Cl | H |
| 35 | 3-CF$_3$ | 5-F | H |

COMPOUND OF EXAMPLE 30

(2S)-2-{[4-Methoxy-3-(N-{[4-(3,5-dichlorophenoxy)phenyl]methyl}carbamoyl)phenyl]methyl}butyric Acid Mp: 145-148° C. $^1$H-NMR (400 MHz, CDCl$_3$, δ): 0.97 (3H, t, J 7.6), 1.56-1.71 (2H, m), 2.60-2.67 (1H, m), 2.79 (1H, dd, J 6.4, 13.8), 2.95 (1H, dd, J 8.8, 13.8), 3.92 (3H, s), 4.67 (2H, d, J 6.0), 6.85-6.86 (2H, m), 6.89-6.91 (1H, m), 7.00-7.02 (2H, m), 7.06-7.07 (1H, m), 7.26-7.30 (1H, m), 7.37-7.39 (2H, m), 8.08-8.09 (1H, m), 8.27 (1H, brs). HRMS: found 501.1104 (−0.5 mmu). Anal: Calcd for C$_{26}$H$_{25}$Cl$_2$NO$_5$ C, 62.16; H, 5.02; N, 2.79; found C, 62.30; H, 5.08; N, 2.75. [α]$_D^{25}$: +18.0°.

COMPOUND OF EXAMPLE 31

(2S)-2-{[4-Methoxy-3-(N-{[4-(3,4-dichlorophenoxy)phenyl]methyl}carbamoyl)phenyl]methyl}butyric acid Mp: 139-141° C. $^1$H-NMR (400 MHz, CDCl$_3$, δ): 0.96 (3H, t, J 7.6), 1.55-1.75 (2H, m), 2.59-2.67 (1H, m), 2.79 (1H, dd, J 6.0, 13.6), 2.95 (1H, dd, J 8.8, 13.6), 3.92 (3H, s), 4.66 (2H, d, J 6.0), 6.83-6.86 (1H, m), 6.89-6.91 (1H, m), 6.97-7.00 (2H, m), 7.06-7.07 (1H, m), 7.26-7.30 (1H, m), 7.35-7.37 (3H, m), 8.08 (1H, m), 8.26 (1H, brs). HRMS: found 501.1080 (−3.0 mmu). Anal: Calcd for C$_{26}$H$_{25}$Cl$_2$NO$_5$ C, 62.16; H, 5.02; N, 2.79; found C, 62.26; H, 5.07; N, 2.81; [α]$_D^{25}$: +21.4°.

COMPOUND OF EXAMPLE 32

(2S)-2-{[4-Methoxy-3-(N-{[4-(4-chloro-3-fluorophenoxy)phenyl]methyl}carbamoyl)phenyl]methyl}butyric acid Mp: 117-118° C. $^1$H-NMR (400 MHz, CDCl$_3$, δ): 0.96 (3H, t, J 7.6), 1.59-1.70 (2H, m), 2.61-2.64 (1H, m), 2.79 (1H, dd, J 6.8, 13.6), 2.95 (1H, dd, J 8.8, 13.6), 3.92 (3H, s), 4.66 (2H, d, J 6.0), 6.72-6.79 (2H, m), 6.89-6.91 (1H, m), 6.99-7.01 (2H, m), 7.26-7.37 (4H, m), 8.07-8.08 (1H, m), 8.26 (1H, brs). HRMS: found 485.1391 (−1.5 mmu). Anal: Calcd for C$_{26}$H$_{25}$ClFNO$_5$ C, 64.26; H, 5.19; N, 2.88; found C, 64.13; H, 5.24; N, 2.93 [α]$_D^{25}$: +24.1°.

COMPOUND OF EXAMPLE 33

(2S)-2-{[4-Methoxy-3-(N-{[4-(4-bromo-3-chlorophenoxy)phenyl]methyl}carbamoyl)phenyl]methyl}butyric acid Mp: 140-142° C. $^1$H-NMR (400 MHz, CDCl$_3$, δ): 0.96 (3H, t, J 7.6), 1.56-1.72 (2H, m), 2.60-2.67 (1H, m), 2.79 (1H, dd, J 6.4, 13.6), 2.95 (1H, dd, J 8.8, 13.6), 3.92 (3H, s), 4.66 (2H, d, J 5.6), 6.76-6.79 (1H, m), 6.89-6.91 (1H, m), 6.98-7.01 (2H, m), 7.07-7.08 (1H, m), 7.27-7.30 (1H, m), 7.35-7.37 (2H, m), 7.51-7.53 (1H, m), 8.07-8.08 (1H, m), 8.26 (1H, brs). HRMS: found 545.0588 (−1.7 mmu). Anal: Calcd for C$_{26}$H$_{25}$BrClNO$_5$ C, 57.11; H, 4.61; N, 2.56; found C, 57.20; H, 4.65; N, 2.57. [α]$_D^{25}$: +21.4°.

COMPOUND OF EXAMPLE 34

(2S)-2-{[4-Methoxy-3-(N-{[4-(4-chloro-3-trifluoromethylphenoxy)phenyl]methyl}carbamoyl)phenyl]methyl}butyric acid Mp: 141-142° C. $^1$H-NMR (400 MHz, CDCl$_3$, δ): 0.97 (3H, t, J 7.2), 1.56-1.72 (2H, m), 2.60-2.67 (1H, m), 2.79 (1H, dd, J 6.4, 13.6), 2.95 (1H, dd, J 8.8, 13.6), 3.92 (3H, s), 4.67 (2H, d, J 6.4), 6.89-6.91 (1H, m), 6.98-7.00 (2H, m), 7.05-7.08 (1H, m), 7.25-7.31 (2H, m), 7.37-7.43 (3H, m), 8.08 (1H, m), 8.27 (1H, brs). HRMS: found 535.1388 (−1.5 mmu). Anal: Calcd for C$_{27}$H$_{25}$ClF$_3$NO$_5$ C, 60.57; H, 4.70; N, 2.61; found C, 60.44; H, 4.71; N, 2.67. [α]$_D^{25}$: +25.9°.

COMPOUND OF EXAMPLE 35

(2S)-2-{[4-Methoxy-3-(N-{[4-(3-fluoro-5-trifluoromethylphenoxy)phenyl]methyl}carbamoyl)phenyl]methyl}butyric acid Mp: 125-128° C. $^1$H-NMR (400 MHz, CDCl$_3$, δ): 0.97 (3H, t, J 7.6), 1.56-1.72 (2H, m), 2.60-2.67 (1H, m), 2.79 (1H, dd, J 6.8, 14.0), 2.95 (1H, dd, J 8.4, 14.0), 3.92 (3H, s), 4.68 (2H, d, J 5.2), 6.81-6.85 (1H, m), 6.89-6.91 (1H, m), 7.00-7.04 (4H, m), 7.27-7.30 (1H, m), 7.39-7.41 (2H, m), 8.08-8.09 (1H, m), 8.28 (1H, brs). HRMS: found 519.1694 (−2.5 mmu). Anal: Calcd for C$_{27}$H$_{25}$F$_4$NO$_5$C, 62.43; H, 4.85; N, 2.70; found, 62.34; H, 4.88; N, 2.77. [α]$_D^{25}$: +22.6°.

REFERENTIAL EXAMPLE 1

N-[4-(3,4-Difluorophenoxy)phenylmethyl]phthalimide

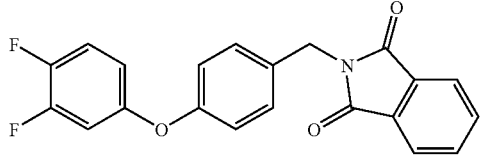

1) Process 1

4-(3,4-Difluorophenoxy)benzyl alcohol

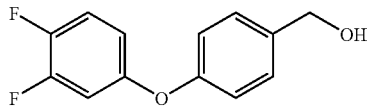

To a solution of 4-fluorobenzaldehyde (2.50 g, 20.1 mmol) in N,N-dimethylformamide (13 mL) were added potassium carbonate (3.33 g, 24.1 mmol) and 3,4-difluorophenol (2.61 g, 20.1 mmol) in turn, and the mixture was stirred for 2.5 hours at 135° C. Water was added to the reaction mixture, which was extracted with ethyl acetate. Then the ethyl acetate layer was washed with brine, dried over anhydrous magnesium sulfate, and then concentrated under reduced pressure. To the residue were added ethanol (50 mL) and sodium borohydride (760 mg, 20.1 mmol) in turn, and the mixture was stirred for 4 hours at room temperature. Water was added to the reaction mixture, which was brought to pH 4 with 3 mol/L hydrochloric acid and extracted with ethyl acetate. The ethyl acetate layer was washed with saturated aqueous solution of sodium hydrogencarbonate and brine, dried over anhydrous magnesium sulfate, and then concentrated. The residue was purified by silica gel column chromatography (hexane:ethyl acetate=20:1→3:1) to afford 4.40 g of pale yellow liquid title compound. Yield 93%.

$^1$H-NMR (400 MHz, CDCl$_3$, δ): 4.69 (2H, d, J 5.9), 6.72-6.74 (1H, m), 6.80-6.85 (1H, m), 7.00 (2H, d, J 8.8), 7.11 (1H, q, J 9.3), 7.37 (2H, d, J 8.8).

2) Process 2

N-[4-(3,4-Difluorophenoxy)phenylmethyl]phthalimide

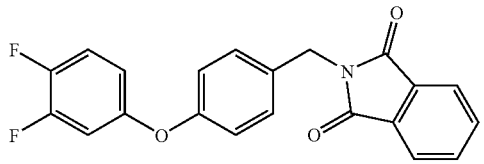

To a solution of compound (4.40 g, 18.6 mmol) obtained in Process 1 in dichloromethane (10 mL) was added thionyl chloride (2.65 g, 22.3 mmol), and the mixture was stirred for 2 hours at room temperature. The reaction mixture was concentrated under reduced pressure and N,N-dimethylformamide (15 mL) and potassium phthalimide (3.61 g, 19.5 mmol) were added to the residue in turn, which was stirred for 2 hours at 80° C. Water was added to the reaction mixture, the precipitated powder was collected by filtration, which was washed with water and then dried to afford 6.52 g of white powdery title compound. Yield 96%.

$^1$H-NMR (400 MHz, CDCl$_3$, δ): 4.83 (2H, s), 6.67-6.71 (1H, m), 6.77-6.82 (1H, m), 6.93 (2H, d, J 8.3), 7.09 (1H, q, J 9.3), 7.44 (2H, d, J 8.3), 7.70-7.74 (2H, m), 7.84-7.88 (2H, m).

REFERENTIAL EXAMPLES 2 THROUGH 8

Through similar process to Referential example 1, compounds listed in following Table 6 were obtained.

TABLE 6

| Ref. example | R1 | R2 | R3 |
|---|---|---|---|
| 2 | 3-F | 5-F | H |
| 3 | 2-F | 3-F | H |
| 4 | 2-F | 4-F | H |
| 5 | 2-F | 5-F | H |
| 6 | 2-F | 6-F | H |
| 7 | 3-F | 4-F | 5-F |
| 8 | 3-CF$_3$ | 5-CF$_3$ | H |

COMPOUND OF REFERENTIAL EXAMPLE 2

N-[4-(3,5-Difluorophenoxy)phenylmethyl]phthalimide $^1$H-NMR (400 MHz, CDCl$_3$, δ): 4.85 (2H, s), 6.43-6.53 (3H, m), 7.00 (2H, d, J 8.8), 7.47 (2H, d, J 8.8), 7.73 (2H, m), 7.87 (2H, m).

COMPOUND OF REFERENTIAL EXAMPLE 3

N-[4-(2,3-Difluorophenoxy)phenylmethyl]phthalimide $^1$H-NMR (400 MHz, CDCl$_3$, δ): 4.82 (2H, s), 6.73-6.78 (1H, m), 6.91-7.02 (4H, m), 7.43 (2H, d, J 8.8), 7.69-7.74 (2H, m), 7.83-7.87 (2H, m).

COMPOUND OF REFERENTIAL EXAMPLE 4

N-[4-(2,4-Difluorophenoxy)phenylmethyl]phthalimide $^1$H-NMR (400 MHz, CDCl$_3$, δ): 4.81 (2H, m), 6.80-6.88 (2H, m), 6.90-6.96 (1H, m), 7.00-7.05 (1H, m), 7.40 (2H, d, J 8.8), 7.70-7.73 (2H, m), 7.82-7.86 (2H, m).

COMPOUND OF REFERENTIAL EXAMPLE 5

N-[4-(2,5-Difluorophenoxy)phenylmethyl]phthalimide $^1$H-NMR (400 MHz, CDCl$_3$, δ): 4.83 (2H, s), 6.68-6.72 (1H, m), 6.74-6.80 (1H, m), 6.95 (2H, d, J 8.8), 7.08-7.14 (1H, m), 7.44 (2H, d, J 8.8), 7.71-7.73 (2H, m), 7.84-7.87 (2H, m).

COMPOUND OF REFERENTIAL EXAMPLE 6

N-[4-(2,6-Difluorophenoxy)phenylmethyl]phthalimide $^1$H-NMR (400 MHz, CDCl$_3$, δ): 4.80 (2H, s), 6.87 (2H, d, J 8.8), 6.95-7.02 (2H, m), 7.10-7.18 (2H, m), 7.40 (2H, d, J 8.8), 7.68-7.72 (2H, m), 7.82-7.86 (2H, m).

COMPOUND OF REFERENTIAL EXAMPLE 7

N-[4-(3,4,5-Trifluorophenoxy)phenylmethyl]phthalimide $^1$H-NMR (400 MHz, CDCl$_3$, δ): 4.84 (2H, s), 6.55-6.59 (2H, m), 6.96 (2H, d, J 8.8), 7.47 (2H, d, J 8.8), 7.72-7.74 (2H, m), 7.85-7.88 (2H, m).

COMPOUND OF REFERENTIAL EXAMPLE 8

N-{4-[3,5-Bis(trifluoromethyl)phenoxy]phenylmethyl}phthalimide

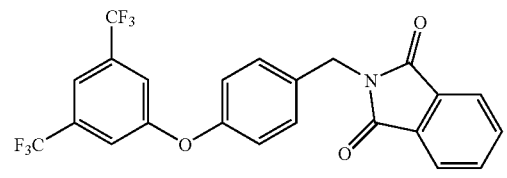

$^1$H-NMR (400 MHz, CDCl$_3$, δ): 4.86 (2H, s), 7.00 (2H, d, J 8.8), 7.37 (2H, s), 7.51 (2H, d, J 8.8), 7.56 (1H, s), 7.72-7.74 (2H, m), 7.86-7.88 (2H, m).

REFERENTIAL EXAMPLES 9 THROUGH 14

Through similar process to Referential example 1, compounds listed in following Table 7 were obtained.

TABLE 7

| Ref. example | R1 | R2 | R3 |
|---|---|---|---|
| 9 | 3-Cl | 5-Cl | H |
| 10 | 3-Cl | 4-Cl | H |
| 11 | 3-F | 4-Cl | H |
| 12 | 3-Cl | 4-Br | H |
| 13 | 3-CF$_3$ | 4-Cl | H |
| 14 | 3-CF$_3$ | 5-F | H |

COMPOUND OF REFERENTIAL EXAMPLE 9

N-[4-(3,5-Dichlorophenoxy)phenylmethyl]phthalimide $^1$H-NMR (400 MHz, CDCl$_3$, δ): 4.84 (2H, s), 6.83-6.84 (2H, m), 6.96-6.98 (2H, m), 7.05-7.06 (1H, m), 7.45-7.48 (2H, m), 7.71-7.73 (2H, m), 7.85-7.88 (2H, m).

COMPOUND OF REFERENTIAL EXAMPLE 10

N-[4-(3,4-Dichlorophenoxy)phenylmethyl]phthalimide $^1$H-NMR (400 MHz, CDCl$_3$, δ): 4.83 (2H, s), 6.81-6.84 (1H, m), 6.94-6.96 (2H, m), 7.05-7.06 (1H, m), 7.33-7.36 (1H, m), 7.44-7.46 (2H, m), 7.71-7.85 (2H, m), 7.86-7.87 (2H, m).

COMPOUND OF REFERENTIAL EXAMPLE 11

N-[4-(4-Chloro-3-fluorophenoxy)phenylmethyl]phthalimide $^1$H-NMR (400 MHz, CDCl$_3$, δ): 4.84 (2H, s), 6.69-6.77 (2H, m), 6.95-6.97 (2H, m), 7.27-7.31 (1H, m), 7.44-7.46 (2H, m), 7.71-7.85 (2H, m), 7.86-7.87 (2H, m).

COMPOUND OF REFERENTIAL EXAMPLE 12

N-[4-(4-Bromo-3-chlorophenoxy)phenylmethyl]phthalimide $^1$H-NMR (400 MHz, CDCl$_3$, δ): 4.84 (2H, s), 6.74-6.77 (2H, m), 6.94-6.96 (2H, m), 7.06 (1H, m), 7.44-7.46 (2H, m), 7.49-7.52 (1H, m), 7.71-7.73 (2H, m), 7.85-7.87 (2H, m).

COMPOUND OF REFERENTIAL EXAMPLE 13

N-[4-(4-Chloro-3-trifluoromethylphenoxy)phenylmethyl]phthalimide $^1$H-NMR (400 MHz, CDCl$_3$, δ): 4.84 (2H, s), 6.94-6.96 (2H, m), 7.02-7.05 (1H, m), 7.30-7.31 (1H, m), 7.39-7.41 (1H, m), 7.45-7.47 (2H, m), 7.72-7.74 (2H, m), 7.85-7.87 (2H, m).

COMPOUND OF REFERENTIAL EXAMPLE 14

N-[4-(3-Fluoro-5-trifluoromethylphenoxy)phenylmethyl]phthalimide $^1$H-NMR (400 MHz, CDC$_1$, δ): 4.85 (2H, s), 6.78-6.82 (1H, m), 6.98-7.03 (4H, m), 7.48-7.50 (2H, m), 7.72-7.75 (2H, m), 7.86-7.88 (2H, m).

TEST EXAMPLE 1

Test of Transcriptional Activation on Human Peroxisome Proliferator-activated Receptor (PPAR) α

The CHO cells were cultured in a Dulbecco-modified Eagle's medium containing 10% delipid fetal calf serum (FCS/DMEM). To these cells were cotransfected receptor plasmid and its reporter plasmid (STRATAGENE Corp.) that express fused protein of DNA-binding domain being transcription factor of yeast with ligand-binding domain of human PPARα (Biochemistry, 1993, 32, 5598), and luciferase plasmid of Renilla (Promega Corp.) for internal standard, using lipofectamine. Thereafter, testing compound or (8S)-HETE being a control compound was added in the 10% SFCS/DMEM and both luciferase activities were measured after 24 hours, which were corrected with internal standard.

[Result]

Activity table 1 shows the EC$_{50}$ values of testing compounds (representative compounds among compounds obtained in the examples aforementioned) and control compound.

<Activity table 1>

| Testing compound | Transcriptional activation on PPARα EC$_{50}$ (μmol/L) |
|---|---|
| Example 9 | 0.0016 |
| Example 10 | 0.0029 |
| Example 16 | 0.0023 |
| (8S)-HETE | 1.30 |

From the results as above, it is seen that the inventive (2S)-2-ethylphenylpropanoic acid derivatives have potent transcriptional activation on human peroxisome proliferator-activated receptor α.

TEST EXAMPLE 2

Test of Lipid-lowering Effect

To a 27-month old male Beagle dog (HRA Beagle; Convance Research Products Inc.) was orally administered testing compound (0.3 mg/mL) in weak aqueous alkali solution sealed in a gelatin capsule once a day for continuous 14 days (0.03 mg/kg/day). For the feed during the period of administration, standard diet (Canine diet, PMI nutrition International Inc.) was used. Blood was collected before start of administration and after administration for 14 days, and total cholesterol value in serum and triglyceride value were measured by enzymic method [Cholesterol E-Test Wako (Wako Pure Chemical Industries,Ltd.), Liquitec TGII reagent 1, 2 (Rosch) and standard serum for measurement of lipid (Rosch) were used]. The decreasing rates of total cholesterol value and triglyceride value were calculated, respectively, according to following calculation formula.

Decreasing rate (%)=(Measured value before administration−Measured value after administration)/Measured value before administration×100

[Result]

Activity table 2 shows the decreasing rates of total cholesterol value and triglyceride value in-blood of testing compound (representative compound among compounds obtained in the examples aforementioned).

<Activity table 2>

| | Decreasing rate | |
|---|---|---|
| Testing compound | Total cholesterol | Triglyceride |
| Example 10 | 28 | 50 |

From the results as above, it is seen that the inventive (2S)-2-ethylphenylpropanoic acid derivative has excellent lipid-lowering effect in vivo.

UTILIZABILITY IN THE INDUSTRY

The inventive compounds are novel (2S)-2-ethylphenylpropanoic acid derivatives and their salts, and they exhibit excellent transcriptional activation on PPARα and exhibit excellent lipid-lowering effect in vivo.

Hence, the inventive compounds are effective as lipid-lowering drugs, inhibitory drugs for the progress of the arteriosclerosis and preventive and/or therapeutic drugs for the diabetes.

The invention claimed is:

1. A (2S)-2-Ethylphenylpropanoic acid compound represented by general formula (1-b):

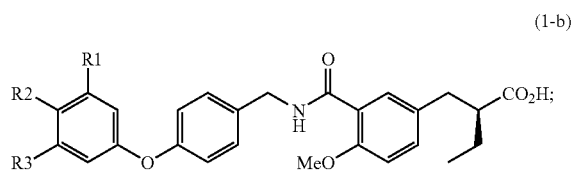

(1-b)

wherein
R1 denotes a halogen atom or trifluoromethyl group,
R2 denotes a hydrogen atom, halogen atom or trifluoromethyl group, and
when R2 denotes a hydrogen atom, R3 denotes a halogen atom or trifluoromethyl group and,
when R2 denotes a halogen atom or trifluoromethyl group, R3 denotes a hydrogen atom, halogen atom or trifluoromethyl group; or a salt thereof.

2. The compound of claim 1, wherein R1, R2 and R3 are, independently, halogen atoms or trifluoromethyl groups; or a salt thereof.

3. The compound of claim 1, wherein R1 and R2 are, independently, halogen atoms or trifluoromethyl groups; and R3 is hydrogen; or a salt thereof.

4. The compound of claim 1, wherein R1 and R3, independently, are halogen atoms or trifluoromethyl groups, and R2 is hydrogen; or a salt thereof.

5. A composition comprising at least one compound of claim 1 or salt thereof which agonizes PPARα.

6. A composition comprising at least one compound of claim 1 or salt thereof which has dual agonist activity on PPARα and PPARγ.

7. A composition comprising at least one compound of claim 1 or a salt thereof which has dual agonist activity on PPARα and PPARδ.

8. A composition comprising at least one compound of claim 1 or a salt thereof which has triple agonist activity on PPARα, PPARγ and PPARδ.

9. A pharmaceutical composition comprising at least one compound of claim 1 or its salt and a pharmaceutically acceptable carrier or excipient.

10. A method for reducing lipids comprising administering to a subject in need thereof an effective amount of at least one compound of claim 1 or its salt.

11. A method for treating arteriosclerosis comprising administering to a subject in need thereof an effective amount of at least one compound of claim 1 or its salt.

12. The method of claim 10 wherein the subject has diabetes.

13. A method for treating obesity comprising administering to a subject in need thereof an effective amount of at least one compound of claim 1 or its salt.

14. The method of claim 10 wherein said subject has syndrome X.

15. The compound of claim 3, or its salt, selected from the group consisting of (2S)-2-{[3-(N-{[4-(3,5-bistrifluoromethylphenoxy)phenyl]methyl}carbamoyl)-4-methoxyphenyl]methyl}butyric acid, (2S)-2-{[3-(N-{[4-(3-bromo-5-chlorophenoxy)phenyl]methyl}carbamoyl)-4-methoxyphenyl]methyl}butyric acid, (2S)-2-{[3-(N-{[4-(3-bromo-5-fluorophenoxy)phenyl]methyl}carbamoyl)-4-methoxyphenyl]methyl}butyric acid, (2S)-2-{[3-(N-{[4-(3-bromo-5-trifluoromethylphenoxy)phenyl]methyl}carbamoyl)-4-methoxyphenyl]methyl}butyric acid, (2S)-2-{[3-(N-{[4-(3-chloro-5-fluorophenoxy)phenyl]methyl}carbamoyl)-4-methoxyphenyl]methyl}butyric acid, (2S)-2-{[3-(N-{[4-(3-chloro-5-trifluoromethylphenoxy)phenyl]methyl}carbamoyl)-4-methoxyphenyl]methyl}butyric acid, (2S)-2-{[3-(N-{[4-(3-fluoro-5-trifluoromethylphenoxy)phenyl]methyl}carbamoyl)-4-methoxyphenyl]methyl}butyric acid, (2S)-2-{[3-(N-{[4-(3,5-dibromophenoxy)phenyl]methyl}carbamoyl)-4-methoxyphenyl]methyl}butyric acid, (2S)-2-{[3-(N-{[4-(3,5-dichlorophenoxy)phenyl]methyl}carbamoyl)-4-methoxyphenyl]methyl}butyric acid, (2S)-2-{[3-(N-{[4-(3,5-difluorophenoxy)phenyl]methyl}carbamoyl)-4-methoxyphenyl]methyl}butyric acid,(2S)-2-{[3-(N-{[4-(3,4,5-trichlorophenoxy)phenyl]methyl}carbamoyl)-4-methoxyphenyl]methyl}butyric acid, and (2S)-2-{[3-(N-{[4-(3,4,5-trifluorophenoxy)phenyl]methyl}carbamoyl)-4-methoxyphenyl]methyl}butyric acid, or the corresponding salts thereof.

16. A method for reducing lipids or a method for treating arteriosclerosis, obesity, comprising administering to a subject in need thereof an effective amount of the compound of claim 15.

17. The compound of claim 2, wherein R1, R2 and R3 are all halogen, or wherein R1, R2 and R3 are all trifluoromethyl.

18. The compound of claim 3, wherein R1 and R2 are each halogen, or wherein R1 and R2 are each trifluoromethyl.

19. The compound of claim 4, wherein R1 and R3 are each halogen, or wherein R1 and R3 are each trifluoromethyl.

* * * * *